(12) United States Patent
DiPiano et al.

(10) Patent No.: US 8,226,972 B2
(45) Date of Patent: *Jul. 24, 2012

(54) VAGINAL DELIVERY OF DRUGS

(75) Inventors: Gerianne Tringali DiPiano, Malvern, PA (US); John A. Ziemniak, Gwynedd Valley, PA (US); Thomas Janicki, South Euclid, OH (US)

(73) Assignee: FemmePharma Holding Company, Inc., Wayne, PA (US)

( * ) Notice: Subject to any disclaimer, the term of this patent is extended or adjusted under 35 U.S.C. 154(b) by 952 days.

This patent is subject to a terminal disclaimer.

(21) Appl. No.: 10/324,624

(22) Filed: Dec. 19, 2002

(65) Prior Publication Data

US 2003/0143278 A1    Jul. 31, 2003

Related U.S. Application Data

(60) Provisional application No. 60/342,663, filed on Dec. 20, 2001.

(51) Int. Cl.
  A61F 6/06    (2006.01)
  A61F 13/02   (2006.01)
  A61F 6/14    (2006.01)
(52) U.S. Cl. ........ 424/430; 424/431; 424/432; 424/433; 424/434
(58) Field of Classification Search .................. 424/430, 424/431, 432, 433, 434
See application file for complete search history.

(56) References Cited

U.S. PATENT DOCUMENTS

| | | |
|---|---|---|
| 3,921,636 A | 11/1975 | Zaffaroni |
| 3,927,216 A | 12/1975 | Witkowski et al. |
| 4,081,533 A | 3/1978 | Cheesman |
| 4,107,288 A | 8/1978 | Oppenheim et al. |
| 4,272,398 A | 6/1981 | Jaffe |
| 4,286,587 A | 9/1981 | Wong |
| 4,291,028 A | 9/1981 | Vorys |
| 4,292,315 A | 9/1981 | Vorys |
| 4,391,797 A | 7/1983 | Folkman et al. |
| 4,524,359 A | 6/1985 | Champagne |
| 4,525,340 A | 6/1985 | Lange et al. |
| 4,588,724 A | 5/1986 | Greenway, III et al. |
| 4,591,496 A | 5/1986 | Cohen et al. |
| 4,673,405 A | 6/1987 | Guittard et al. |
| 4,756,907 A | 7/1988 | Beck et al. |
| 4,762,717 A | 8/1988 | Crowly, Jr. |

(Continued)

FOREIGN PATENT DOCUMENTS

DE    100 54 294    5/2002

(Continued)

OTHER PUBLICATIONS

Resnick, Management of Urinary INcontinence in the Elderly, N Engl J Med 1985; 313:800-805Sep. 26, 1985.*

(Continued)

Primary Examiner — Carlos A. Azpuru
(74) Attorney, Agent, or Firm — Pabst Patent Group LLP

(57) ABSTRACT

Drug delivery compositions which are suitable for vaginal administration for the treatment of diseases and disorders in the urogenital tract are described. The compositions may be in the form of a tablet, liquid suspension or dispersion, dried powder, topical ointment, cream, foam, suppository, or aerosol.

The drug delivery compositions are administered directly to the vagina and do not require the use of a solid device. This method of administration reduces the systematic levels of the drugs.

7 Claims, 11 Drawing Sheets

U.S. PATENT DOCUMENTS

| | | | |
|---|---|---|---|
| 4,826,830 A | 5/1989 | Han et al. | |
| 4,861,627 A | 8/1989 | Mathiowitz et al. | |
| 4,873,092 A | 10/1989 | Azuma et al. | |
| 4,919,937 A | 4/1990 | Mauvais-Jarvis et al. | |
| 4,919,939 A | 4/1990 | Baker | |
| 4,965,128 A | 10/1990 | Greidanus et al. | |
| 4,997,653 A | 3/1991 | Igarashi et al. | |
| 5,057,317 A | 10/1991 | Iida | |
| 5,066,495 A | 11/1991 | Moro et al. | |
| 5,091,185 A | 2/1992 | Castillo et al. | |
| 5,130,137 A | 7/1992 | Crowley, Jr. | |
| 5,145,684 A | 9/1992 | Liversidge et al. | |
| 5,156,851 A | 10/1992 | Castillo et al. | |
| 5,194,259 A | 3/1993 | Soudant et al. | |
| 5,324,522 A | 6/1994 | Krenning et al. | |
| 5,330,768 A | 7/1994 | Park et al. | |
| 5,340,585 A | 8/1994 | Pike et al. | |
| 5,359,030 A | 10/1994 | Ekwuribe | |
| 5,362,720 A | 11/1994 | Labrie | |
| 5,413,797 A | 5/1995 | Khan et al. | |
| 5,417,982 A | 5/1995 | Modi | |
| 5,434,146 A | 7/1995 | Labrie | |
| 5,438,040 A | 8/1995 | Ekwuribe | |
| 5,472,704 A | 12/1995 | Santus et al. | |
| 5,482,925 A | 1/1996 | Hutsell | |
| 5,482,927 A | 1/1996 | Maniar et al. | |
| 5,494,047 A | 2/1996 | Van Os | |
| 5,510,118 A | 4/1996 | Bosch et al. | |
| 5,536,499 A | 7/1996 | Znaiden et al. | |
| 5,552,160 A | 9/1996 | Liversidge et al. | |
| 5,580,857 A | 12/1996 | Oden | |
| 5,614,212 A | 3/1997 | D'Angelo et al. | |
| 5,633,011 A | 5/1997 | Dong et al. | |
| 5,643,604 A | 7/1997 | Angeles Uribe et al. | |
| 5,651,976 A | 7/1997 | Price et al. | |
| 5,705,170 A | 1/1998 | Kong et al. | |
| 5,778,894 A | 7/1998 | Dorogi et al. | |
| 5,789,442 A * | 8/1998 | Garfield et al. | 514/561 |
| 5,843,509 A | 12/1998 | Calvo Salve et al. | |
| 5,945,109 A | 8/1999 | Schmidt et al. | |
| 5,993,856 A | 11/1999 | Ragavan et al. | |
| 6,071,526 A | 6/2000 | Schmidt et al. | |
| 6,087,351 A | 7/2000 | Nyce | |
| 6,358,539 B1 | 3/2002 | Murad | |
| 6,416,778 B1 | 7/2002 | Ragavan et al. | |
| 6,436,428 B1 * | 8/2002 | Mahashabde et al. | 424/432 |
| 6,482,448 B2 | 11/2002 | Tabor | |
| 6,517,864 B1 | 2/2003 | Orup Jacobsen et al. | |
| 6,652,874 B2 * | 11/2003 | Ragavan et al. | 424/430 |
| 6,743,441 B2 | 6/2004 | Sanders et al. | |
| 6,908,623 B2 | 6/2005 | Deaver et al. | |
| 2003/0109507 A1 | 6/2003 | Franke et al. | |
| 2003/0143278 A1 | 7/2003 | DiPiano et al. | |
| 2003/0175329 A1 | 9/2003 | Azarnoff et al. | |
| 2004/0002503 A1* | 1/2004 | Chang et al. | 514/255.04 |
| 2004/0018991 A1 | 1/2004 | Schmidt et al. | |
| 2004/0138314 A1 | 7/2004 | Bua | |
| 2004/0229813 A1 | 11/2004 | DiPiano et al. | |
| 2008/0153789 A1 | 6/2008 | Dmowski et al. | |

FOREIGN PATENT DOCUMENTS

| | | |
|---|---|---|
| EP | 0 501 056 | 9/1992 |
| EP | 0 566 135 | 10/1993 |
| GB | 767 824 | 2/1957 |
| JP | 61-500914 | 5/1986 |
| JP | 03-090029 | 3/2003 |
| WO | WO 91/12007 | 8/1991 |
| WO | WO 95/07071 | 3/1995 |
| WO | WO 95/31973 | 11/1995 |
| WO | WO 95/31974 | 11/1995 |
| WO | WO 96/00567 | 1/1996 |
| WO | WO 96/25150 | 8/1996 |
| WO | WO 96/37232 | 11/1996 |
| WO | WO 97/29735 | 8/1997 |
| WO | WO 98/11888 | 3/1998 |
| WO | WO 98/32422 | 7/1998 |
| WO | WO 99/24041 | 5/1999 |
| WO | WO 00/27372 | 5/2000 |
| WO | WO 00/72883 | 12/2000 |
| WO | WO 02/17926 | 3/2002 |
| WO | WO 03/039553 | 5/2003 |
| WO | 03053292 | 7/2003 |

OTHER PUBLICATIONS

Anderson, et al., "Once daily controlled versus immediate release oxybutynin chloride for urge urinary incontinence. OROS Oxybutynin Study Group," J. Urol. 161: 1809-1812 (1999).

Brendler, et al., "Topical oxybutynin chloride for relaxation of dysfunctional bladders," J. Urol. 141(6): 1350-52 (1989).

Buyse, et al., "Intravesical oxybutynin for neurogenic bladder dysfunction: less systemic side effects due to reduced first pass metabolism," J. Urol. 160: 892-896 (1998).

Comer & Goa, "Extended-release oxybutynin," Drugs Aging 16: 149-155 (2000).

Geraghty, et al., "The in vitro release of some antimuscarinic drugs from monoolein/water lyotropic crystalline gels," Pharm. Res. 13(8): 1265-1271 (1996).

Goldenberg, "An extended-release formulation of oxybutynin chloride for the treatment of overactive urinary bladder," Clin. Ther. 21(4): 634-642 (1999).

Gupta & Sathyan, "Pharmacokinetics of an oral once-a-day controlled-release oxybutynin formulation compared with immediate-release oxybutynin," J. Clin. Pharmacol. 39: 289-296 (1999).

Massad, et al., "The pharmacokinetics of intravesical and oral oxybutynin chloride," J. Urol. 148: 595-597 (1992).

Saito, et al., "Treatment of overactive bladder with modified intravesical oxybutynin chloride," Neurol. Urodyn. 19: 683-688 (2000).

Schröder, et al., "Absorption of oxybutynin from vaginal inserts: drug blood levels and the response of the rabbit bladder," Urology 56(6): 1063-1067 (2000).

Thüroff, et al., "Randomized, double-blind, multicenter trial on treatment of frequency, urgency and incontinence related to detrusor hyperactivity: oxybutynin versus propantheline versus placebo," J. Urol. 145: 813-816 (1991).

Versi, et al., "Dry mouth with conventional and controlled-release oxybutynin in urinary incontinence," Obstet Gynecol. 95(5): 718-721 (2000).

U.S. Appl. No. 12/497,865, filed Jul. 6, 2009, DiPiano, et al.

Akio, "Danazol Suppository", Patent Abstracts of Japan 15(263): (C-0847) (1989).

Barnhart, et al., "Distribution of a spermicide containing Nonoxynol-9 in the vaginal canal and the upper female reproductive tract", Hum Reprod,. 16(6):1151-4 (2001).

Benita, et al., "Characterization of drug-loaded poly(d,l-lactide) microspheres,"J Pharm Sci 73(12): 1721-1724 (1984).

Braun, et al, "Effect of danazol in vitro and in vivo on monocyte-mediated enhancement of endometrial cell proliferation in women with endometriosis," Fertility and Sterility 62(1): 89-95 (1994).

Chan, et al., "Breast pain: What to do?", The Hong Kong Practitioner,21:573-578 (1999).

Cicinelli, et al., "First uterine pass effect is observed when estradiol is placed in the upper buy not lower third of the vagina", Fertility and Sterility , 81(5):1414-1416 (2004).

Colacurci, et al., "Effects of tibolone on the breast", Eur. J. Obstet. Gynecol. Reprod. Biol.,80(2):235-8 (1998).

De Ziegler, et al., "Administration non-orale de la progesterone: Expériences et avenir de la vole transvaginale," Rev. Med. Suisse Romande pp, 13-28 (1994).

Farquhar, et al., "Management of dysfunctional uterine bleeding," Drugs 44(4): 378-384 (1992).

Fentiman, et al, "Dosage and duration of tamoxifen treatment for mastalgia: a controlled trial," Br J Surg. 75(9): 845-846 (1988).

Fentiman, et al, "Studies of tamoxifen in women with mastalgia," Br. J. Clinical Prac. Sympt. 68: 34-36 (1989).

Fentiman, et al., "Tamoxifen and benign breast problems.", Lancet,2(8567):1070-1072 (1987).

Finnin and Morgan, "Transdermal penetration enhancers: applications, limitations, and potential",J. Pharm. Sci.,88(10):955-8 (1999).

Guerriero, et al., "Influence of vaginal danazol on uterine and brain perfusion during hormonal replacement therapy", Menopause, 8(6); 424-428 (2001) (abstract only).
Hinton, et al., "A double-blind controlled trial of danazol and bromocriptine in the management of severe cyclical breast pain," Br. J. Clin. Practice 40(8): 326-330 (1986).
Holland & Gateley, "Drug therapy of mastalgia. What are the options?" Drugs 48(5): 709-716 (1994).
Hull, et al., "Endometriosis: An enigmatic disease," J Women's Health 5(2): 111-120 (1996).
Igarashi, "A new therapy for pelvic endometriosis and uterien adenomysosis: Local effect of vaginal and intrauterine danazol application," Asia-Oceania J. Obstet. Gynaecol. 16(1): 1-12 (1990).
Irvin & Morrison, "Effectiveness of topical non-steroidal anti-inflammatory drugs in the management of breast pain," J. R. Coll. Edinb. 43(3): 158-159 (1998).
Leonard, et al., "Randomized, double-blind, placebo-controlled, multicenter trial of 6% miltefosine solution, a topical chemotherapy in cutaneous metastases from breast cancer," J. Clin. Oncol. 19: 4150-4159 (2001).
Lim, et al., "Microencapsulation of living cells and tissues," J Pharm. Sci. 70(4): 351-354 (1981).
Liversidge, et al., "Particle size reduction for improvement of oral bioavailability of hydrophobic drugs: I. Absolute oral bioavailability of nanocrystalline danazol in beagle dogs", Int J Pharm., 125:91-97 (1995).
Lobo, et al., "Vaginal route paradox: A direct transport to the uterus," Symposium: The First Uterine Pass Effect, Wyeth-Ayerst International, Inc. (1995).
Lufkin and Ory, "Relative value of transdermal and oral estrogen therapy in various clinical situations", *Mayo Clin. Proc.*, 69(2):131-5 (1994).
Mansel & Dogliotti, "European multicentre trial of bromocriptine in cyclical mastalgia," *Lancet* 335(868): 190-193 (1990).
Mansel, et al., "A double blind trial of the prolactin inhibitor bromocriptine in painful benign breast disease," *Br. J. Surgery* 65(10): 724-27 (1978).
Mansel, et al., "Controlled trial of the antigonadotropin danazol in painful nodular benign breast disease," Lancet 1(8278): 928-933 (1982).
Mathiowitz, et al., "Morphology of polyanhydride microsphere delivery system," Scanning Microscopy 4(2): 329-340 (1990).
Mathiowitz, et al., "Novel microcapsules for delivery systems," Reactive Polymers 6: 275-283 (1987).
Mathiowitz, et al, "Polyanhydride microspheres as drug carriers I. Hot-melt microencapsulation," J Controlled Release 5:13-22 (1987).
Mathiowitz, et al., "Polyanhydride microspheres as drug carriers. II. Microencapsualtion by solvent removal," J Appl. Polymer Sol. 35: 755-774 (1988).
Millet & Dirbas, "Clinical management of breast pain: a review," Obstet. Gynecol. Survey 57(7): 451-461 (2002).
Mizutani, et al., "Danazol concentration in ovary, uterus, and serum and their effect on the hypothalamic-pituitary-ovarian axis during vaginal administration of a danazol suppository," Feritility and Sterility 63(6): 1184-1189 (1995).
Moline, "Pharmacologic strategies for managing premenstrual syndrome", Clin. Pharm., 12(3):181-96 (1993).
Montgomery, et al., "Treatment of severe cyclical mastalgia.", J. R. Soc. Med., 72(7):489-491 (1979).
Nazli, et al, "Controlled trial of the prolactin inhibitor bromocriptine (Parlodel) in the treatment of severe cyclical mastalgia," Br J Clin Pract 43: 322-327 (1989).

*Physicians' Desk Reference*, Consult 1994 Supplements for Revisions, pp. 1372-1375.
Plu-Bureau, et al., "Percutaneous progesterone use and risk of breast cancer: results from a French cohort study of premenopausal women with benign breast disease", Cancer Detect. Prey., 23(4):290-6 (1999).
Ramjee, et al, "Acceptability of Carraguard, a candidate microbicide and methyl cellulose placebo vaginal gels among HIV-positive women and men in Durban, South Africa", AIDS Res Ther. 4:20 pp. 1-10 (2007).
Salib, et al., "Utilization of sodium alginate in drug microencapsulation," Pharmazeutische Industrie 40(11A): 1230-1234 (1978).
Spooner, Classification of Side Effects to Danazol Therapy, Winthrop Laboratories, Surrey, England.
Steinbrunn, at al., "Mastalgia. Tailoring treatment to type of breast pain," Postgraduate Medicine 102(5): 183-184; 187-187; 193-194 (1997).
"Sultrin," Physicians' Desk Reference, 51st ed., pp. 1941 (1997).
Takebayashi, et al., "Danazol suspension injected into the uterine cervix of patients with adenomyosis and myoma. Preliminary study", Gynecol. Obstet. Invest., 39(3):207-11 (1995) (abstract only).
"Terazol 7," Physicians' Desk Reference, 51st ed., pp. 1943 (1997).
Terwogt, et al., "Phase II trial of topically applied miltefosine solution in patients with skin-metastasized breast cancer," Br. J. Cancer 79: 1158-1161 (1999).
*The First Uterine Pass Effect—A new finding for new options in progesterone therapy*, West-Ayerst Internation, Inc. (1995).
Unger, et al., "Hexadecylphosphocholine in the topical treatment of skin metastases in breast cancer patients," *Cancer Treat. Rev.* 17: 243-246 (1990).
Wagner, et al., "The novel progesterone receptor antagonists RTI 3021-012 and RTI 3021-022 exhibit complex glucocorticoid receptor antagonist activities: implications for the development of dissociated antiprogestins", *Endocrinology,* 140(3):1449-58 (1999).
Wellbery, et al., "Diagnosis and treatment of endometriosis", *Am. Fam. Physician,* 60:1753-68 (1999).
Yamashita, et al., "Immunohistochemical determination of endometrial progesterone receptor (PR) content after intrauterine infusion of danazol in rabbits", Nippon Naibunpi Gakkai Zasshi, 69(10):1044-1050 (1993) (abstract only).
Zhang, et al., "Synthesis and progesterone receptor antagonist activities of 6-aryl benzimidazolones and benzothiazolones", *Bioorg. Med. Chem. Lett.,* 11(20):2747-50 (2001).
Janicki and Dmowski, "A multicenter prospective open-label evaluation of the use of intravaginally administered danazol (FP-1096) in patients with moderate to severe pain associated with endometriosis", presented at International Pelvic Pain Society meeting, Aug. 5-7, 2004.
Janicki and Dmowski, et al., "Intravaginal danazol significantly reduces chronic pelvic pan in women with endometriosis", 51st Annual Meeting of the Society for Gynecologic Investigation, Houston Tx., Mar. 25, 2004.
Koch, et al., "A reversed-phase HPLC method to quantitate oxybutynin chloride, benzoic acid and methyl paraben in an intravaginal gel formulation", presented at AAPS meeting 2004.
Mays, et al., "Pelvic and reproductive delivery (PARDEL): Effective regional drug delivery", The American College of Obstetricians and Gynecologists, Oklahoma City, OK, May 2004 meeting.

* cited by examiner

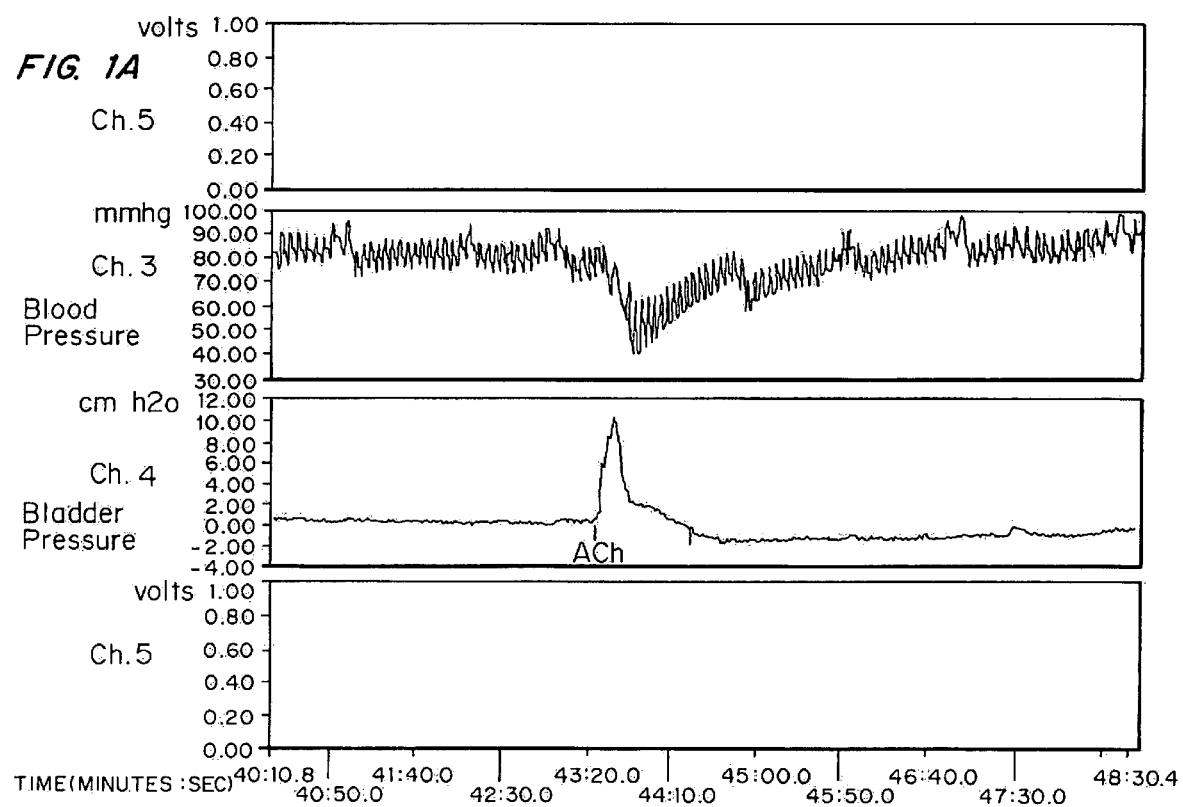

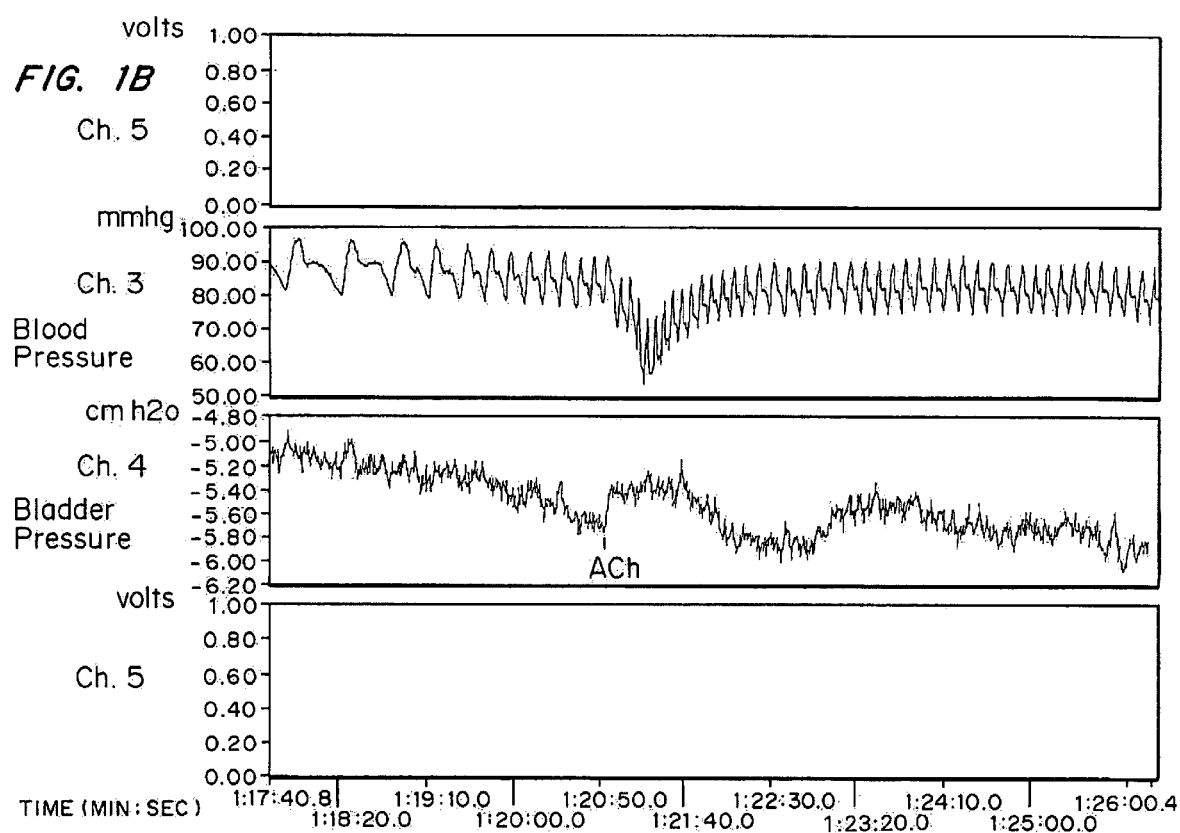

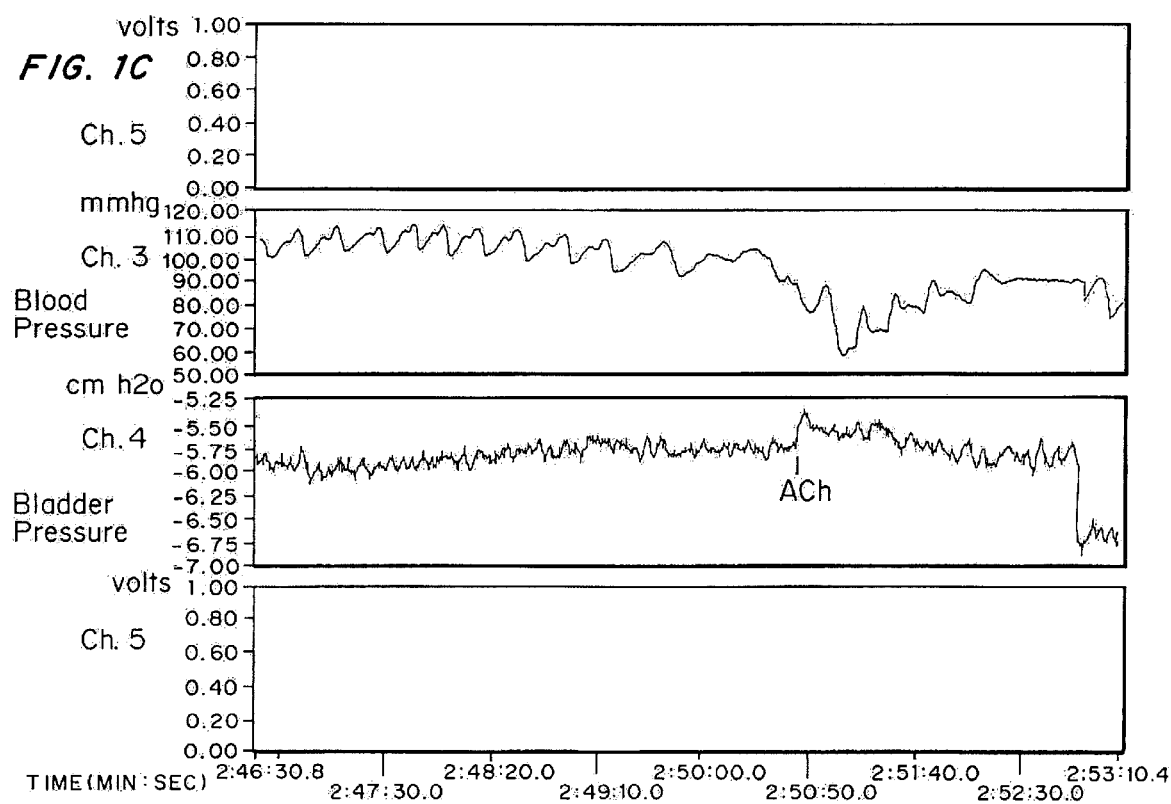

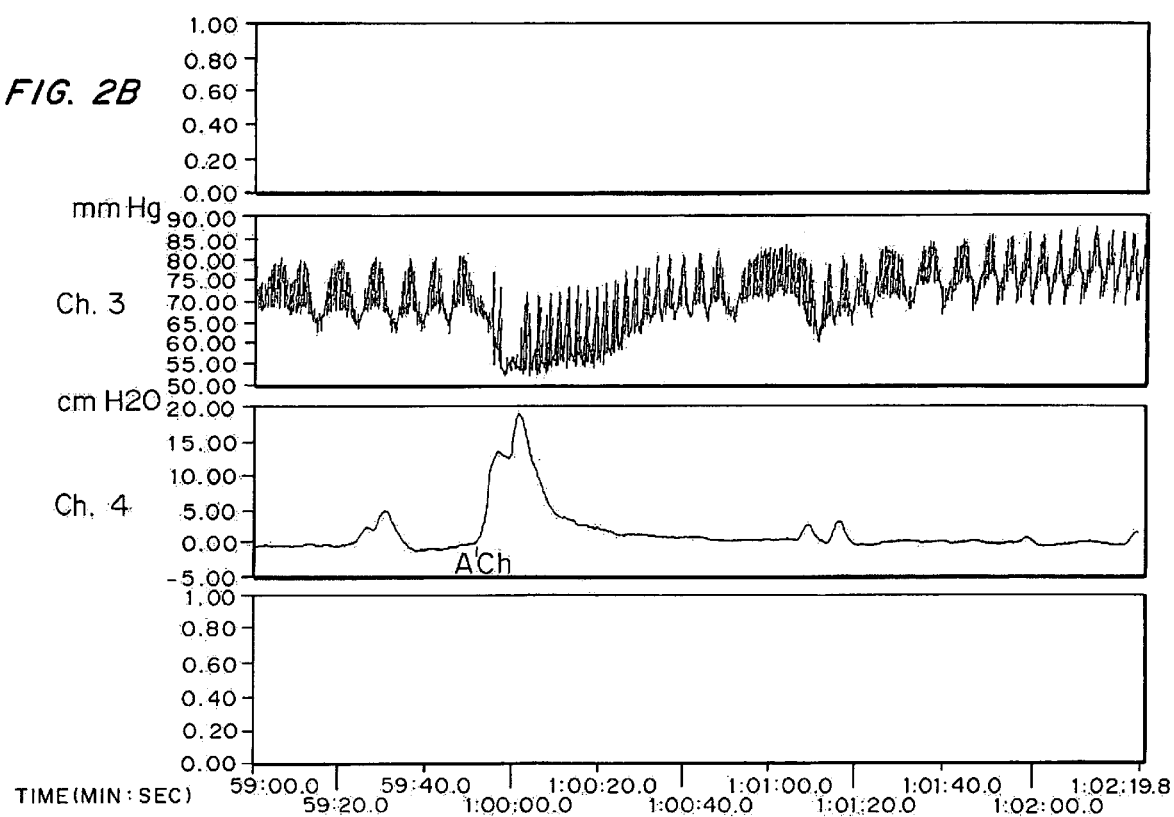

VAGINAL DELIVERY OF DRUGS

PRIORITY CLAIM

This application claims priority to U.S. Ser. No. 60/342,663, entitled "Vaginal Delivery of Drugs", filed Dec. 20, 2001.

BACKGROUND OF THE INVENTION

The present invention relates to pharmaceutical preparations for the treatment of diseases and disorders of the urinogenital tract.

Diseases and disorders of the bladder and urinary tract include cancers, infections, urinary incontinence, urethral syndrome, urethritis, female sexual dysfunction, and interstitial cystitis. These diseases and disorders may be treated by a variety of systemically administered pharmaceutical preparations. However, systemic delivery results in a number of side effects. For example, when oxybutynin hydrochloride is administered orally for the treatment of urinary incontinence, side effects including dizziness, blurred vision, dry mouth, and cardiovascular manifestations are experienced by patients. These side effects often limit the use of the formulation by the patients.

Local application of drugs for the treatment of bladder disorders, such as urinary incontinence, bladder cancer, and interstitial cystitis has been described in the literature. Intravesical administration of doxorubicin for bladder cancer, DMSO for interstitial cystitis, and oxybutynin hydrochloride for urinary incontinence have been shown to provide relief from symptoms without the side effects observed during systemic therapy. However intravesical administration is inconvenient and requires a trained technician to administer the drug formulation. Further, inserting and removing a catheter from a patient increases the risk of patient infection.

The term "urinary incontinence", which refers to the inability to control urine flow, encompasses many different types of incontinence and results from different causes. For example, stress incontinence refers to when leakage of small amounts of urine during physical movement, such as coughing, sneezing, exercising. Urge incontinence generally refers to leakage of large amounts of urine at unexpected times, including during sleep.

Bladder emptying requires the maintenance of pressure in the bladder during the tonic phase of the contractile response. Bladder emptying and continence also depend upon the tonic phase of the contractile responses of the urethra. Thus, a defect in the ability of the bladder to sustain a contraction reduces the ability of the bladder to empty. Similarly, in women, if the urethra is unable to sustain increased tension during bladder filling, stress incontinence may result. Women depend upon urethral smooth muscle tension for continence to a much greater extent than men, where the prostate and better developed external sphincter add significantly to urethral tension and continence.

A second common cause of urinary incontinence is when the bladder contracts during bladder filling, i.e. hyperreflexia. These contractions are primarily due to neurogenic mechanisms involving the release of acetylcholine (herein referred to as "Ach") and muscarinic-modiated bladder contractions.

One agent that has proven to be clinically effective in the treatment of urinary incontinence is oxybutynin. Oxybutynin relaxes the bladder by muscarinic inhibition and by direct relaxation of smooth muscle. Oxybutynin is one of the most widely prescribed oral medications for the treatment of stress incontinence (also referred to as "bladder instability") and urge incontinence (see R. U. Anderson, et al., *J. Urol.*, 161: 1809-1812 (1999); S. K. Gupta & G. Sathyan, *J. Clin. Pharmacol.*, 39: 289-296 (1999); and J. W. Thüroff, et al., *J. Urol.*, 145: 813-816 (1991)). However, its major disadvantages include its relatively short half-life and the resulting anticholinergic side effects. In many cases, patients do not follow their prescribed treatments due to the frequent dosing schedule and the side effects. In order to improve patient compliance, a long-acting preparation (once a day) was developed and tested (M. M. Goldenberg, *Clin Ther,* 21: 634-642 (1999); R. U. Anderson, et al., *J. Urol.,* 161: 1809-1812 (1999);and E. Versi, et al., *Obstet Gynecol.,* 95: 718-721 (2000)). Results of these studies demonstrate that the time-released preparation is as effective as the original preparation, but also produces the side effects associated with the administration of the original formulation (E. Versi, et al., *Obstet Gynecol.,* 95: 718-721 (2000) and A. M. Comer & K. L. Goa, *Drugs Aging,* 16: 149-155 (2000)).

Intravesical instillation of oxybutynin has been evaluated. Brendler describes the intravesical administration of oxybutynin chloride for the treatment of dysfunctional bladders in a study of eleven patients with persistent urge incontinence and frequent side effects from the use of oral anticholinergic agents. (C. B. Brendler et al., *J. Urology,* 141 (6): 1350-52 (June, 1989)) Ten out of eleven patients reported improvement and became totally continent, and no side effects were observed. Similarly, Saito describes using a catheter to deliver an oxybutynin solution to patients suffering from urinary incontinence. (M. Saito et al., *Neurology and Urodynamics* 19: 683-88 (2000)) This method was effective, and the patients did not experience side effects.

Although this method of treatment can avoid the first pass metabolism and reduce systemic side effects (G. Buyse, et al., *J. Urol.,* 160: 892-896 (1998); C. A. Masad, et al., *J. Urol.,* 148: 595-597 (1992)), it is inconvenient and does not provide a method for continuous delivery. Further, intravesical administration requires a trained technician in a medical setting to administer the pharmaceutical preparation using a catheter or some other method of direct instillation into the bladder. Thus, intravesical administration prevents many patients from having daily access to such therapy. Moreover, the use of a catheter or other instrument increases the risk of infection caused by insertion and removal of the instrument and causes the patient discomfort.

A few researchers have begun to investigate vaginal delivery of anticholinergics, such as oxybutynin and propantheline bromide, to the bladder. Geraghty et al., *Pharmaceutical Research* 13(8): 1265-1271 (1996) a formulation containing monoolein and an antimuscarinic drug, either oxybutynin hydrochloride or propantheline bromide. Monoolein is a polar lipid which forms gels in the presence of water. Geraghty performed in vitro experiments to determine if the gel was an effective delivery system for the antimuscarinic drugs. The gel formulations demonstrated a sustained release of the antimuscarinic drugs for approximately 18 hours. Based on the release profile, it appeared that the drug diffused out of the gel. However, such results are not predictive of what would happen in vivo since the gel could degrade or the drug could be delivered systemically.

Schröder A et al., *Urology* 56 (6): 1063-1067 (2000) describes inserting a solid device which contained oxybutynin in the vagina of a rabbit. Though Schröder's insert was effective at reducing the systemic levels of oxybutynin, inserts are often uncomfortable for patients.

It is therefore an object of the present invention to provide formulations and methods of administration that are effective in treating diseases and disorders of the female urogenital system that also increase patient comfort and the likelihood that patients will follow their prescribed treatments.

It is a further object of the present invention to provide formulations and methods of administration that permit uptake of the drug in the affected area with minimal systemic side effects.

BRIEF SUMMARY OF THE INVENTION

Drug delivery compositions which are suitable for vaginal adminisiration for the treatment of diseases and disorders of the urogenital tract are described. The drug delivery compositions are transvaginal formulations that are administered directly to the vagina and do not require the use oh solid device. This method of administration reduces the systemic levels of the drugs end decreases the side effects which are associated with systemic administration. In the preferred embodiment, the compositions are in the form of a dried powder, solution, suppository, ovual, or aerosol. The preferred dosage contains 1-20 mg of drug/administration. In the preferred embodiment, the composition contains an antimuscarino drug, such as oxybutynin.

BRIEF DESCRIPTION OF THE DRAWINGS

FIGS. 1A, B, and C are cystometric curves of the blood pressure (mm Hg) and bladder pressure (cm $H_2O$) responses to acetylcholine (referred to herein as "Ach") before, 15 minutes after, and 4 hours after the administration of a high dose of Oxybutynin (0.5 g Oxybutynin/g gel) in rabbits. FIG. 1A shows a control response of the bladder and blood pressure to Ach. FIG. 1B shows the effect 15 minutes after a high dose of Oxybutynin has been administered. FIG. 1C shows the response 4 hours after a high dose of Oxybutynin was administered.

FIG. 2A shows a control response of the bladder and blood pressure to Ach. FIG. 2B shows the effect 15 minutes after a low dose of Oxybutynin has been administered.

FIG. 5 graphically depicts the effect of the administration of oxybutynin on the response to intra-arterial Ach.

DETAILED DESCRIPTION OF THE INVENTION

I. Drug Delivery Compositions

Figure 2A:
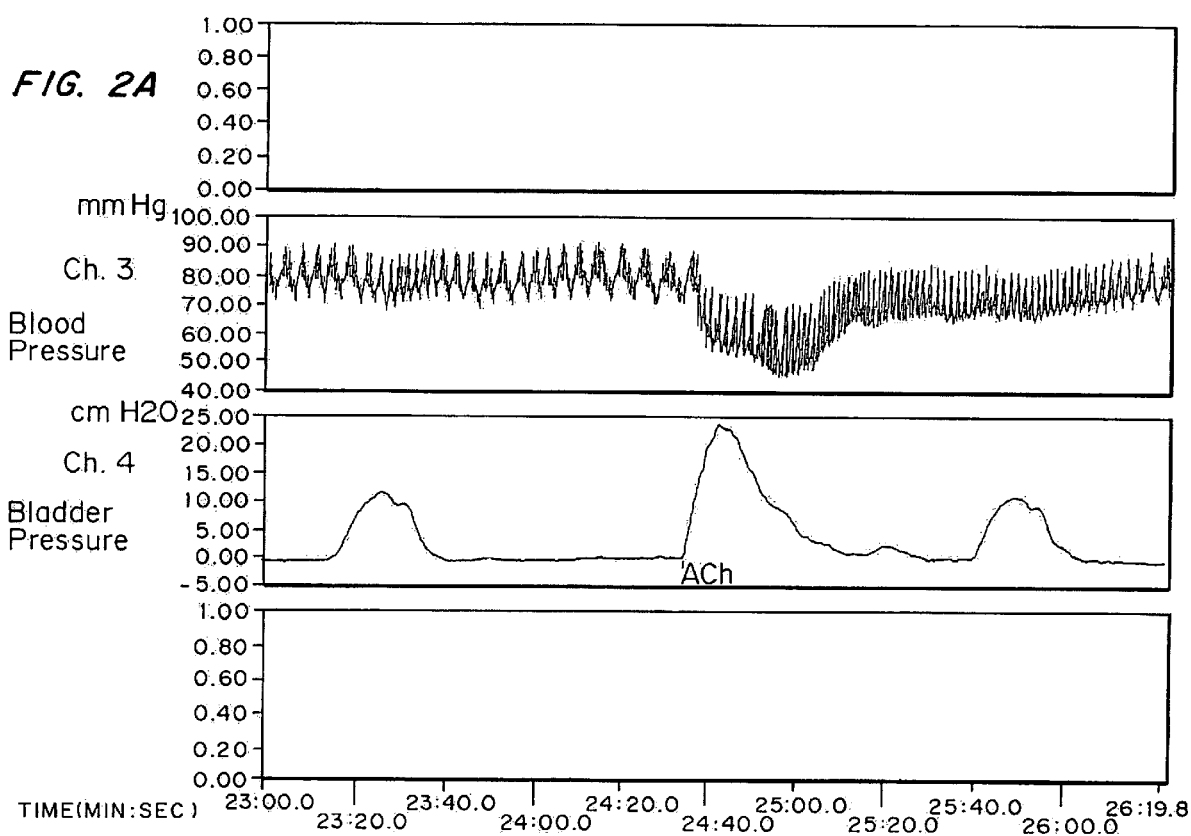
FIGS. 2A, B, and C are cystometric curves of the blood pressure (mm Hg) and bladder pressure (cm $H_2O$) responses to Ach before, 15 minutes after, and 4 hours after the administration of a low dose of Oxybutynin (0.05 g Oxybutynin/g gel) in rabbits.

The drug delivery compositions consist of drug alone or in combination with an excipient or polymeric carrier. The excipient or polymeric carrier may be used to alter the release rate or to increase adhesion in the affected area. The drug formulation may be administered as a dried powder, solution, suppository, ovual, or aerosol.

A. Drug

Drug refers to aqueous soluble drugs or micro- or nanoparticulates of non-soluble drugs, which achieve the desired effect. Drugs can be synthetic or natural organic compounds, proteins or peptides, oligonucleotides or nucleotides, or polysaccharides or sugars. Drugs may have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, or be useful as contrast or other diagnostic agents. A description of classes of drugs and species within each class can be found in Martindale, *The Extra Pharmacopoeia*, 31st Ed., The Pharmaceutical Press, London (1996) and Goodman and Gilman, *The Pharmacological Basis of Therapeutics*, (9th Ed., McGraw-Hill Publishing company (1996)).

Examples of compounds with steroidal activity include progestins, estrogens, antiestrogens and antiprogestins.

The drug may be an α-adrenergic agonist.

The drug may be an antimuscarinic, such as DETROL® LA (tolterodine tartrate) (Pharmacia Corp.), propantheline, and oxybutynin hydrochloride.

B. Carriers and Excipients

The carrier may be an ointment, gel, paste, lotion, sponge, powder, or spray, soft gelatin capsules. The drug may be in a paste or gel which is placed in a soft gelatin capsule.

Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

Polymers can be used to increase adhesion to mucosal surfaces, to control release as a function of the diffusion rate of drugs out of the polymeric matrix and/or rate of degradation by hydrolysis or enzymatic degradation of the polymers and/or pH alteration, and to increase surface area of the drug relative to the size of the particle.

C. Dosage

The compositions are administered to a patient in an amount that contains a dosage in an amount equivalent to approximately one to twenty mg of drug, depending on the activity of the drug. In the preferred embodiment, the formulation contains low dosages of drug, such as up to 5 mg or up to 7 mg. The compositions may result in sustained, continuous release of the drug or immediate, i.e. burst, release of the drug.

II. Methods of Using the Compositions The drug delivery compositions are applied directly to the vagina and result in preferential uptake of the drug by the bladder receptors. The compositions may be in the form of a tablet, solution, dried powder, topical ointment, cream, foam, suppository, ovual, or an aerosol.

The formulations can be used in the treatment of cancers, infections such as infections of the urinary tract, urinary incontinence, urethral syndrome, urethritis, female sexual dysfunction, and interstitial cystitis.

The drug compositions are applied once or twice daily throughout the period that a patient has the disorder, infection, or disease. Approximately 1-20 mg of drug is administered to a patient in each application. In the preferred embodiment, the formulation contains low dosages of drug, such as up to 5 mg or up to 7 mg.

For the treatment of urinary incontinence, the application of the formulations may result in increased bladder capacity and/or decreased Bladder Compliance. Bladder Compliance refers to the change in pressure per unit volume ($\Delta P/V$). Thus a decrease in Bladder Compliance due to the administration of a drug, such as oxybutynin, results when the pressure is lower after the administration of the drug than it was prior to the administration of the drug for the same volume at micturition.

EXAMPLES

Example 1

Study of the Effect of Vaginal Oxybutynin on Bladder Function Using Rabbits 16 mature female New Zealand white rabbits were separated into two groups of eight. The rabbits in Group 1 received a high dose oxybutynin formulations; and the rabbits in Group 2 received a low dose oxybutynin formulation. For the high dose, 3 grams (g) of oxybutynin HCl were suspended in 6 g of gel (yielding a concentration of 0.5 g Oxybutynin/g gel) and 3 g of the formulation were placed in the vagina. For the low dose, 0.3 g of oxybutynin HCl were suspended in 6 g of gel (yielding a concentration of 0.05 g Oxybutynin/g gel), and 3 g of the formulation were placed in the vagina.

Surgical Preparation

Each rabbit was sedated with an intramuscular injection of ketamine-xylazine ((25 mg ketamine+6 mg xylazine)/kg rabbit) and anesthesia was maintained by isoflurane. After anesthesia, the right external carotid artery was cannulated for blood pressure monitoring. A polyethylene catheter (Intramedic) with an outer diameter of 0.043 inches was inserted through the rabbit's right femoral artery until it reached the lower abdominal aorta (approximately 0.5 cm above the bifurcation of the aorta). A heparizined saline (30 iu/mL) filled polyethylene catheter was used for intra-arterial administration of drugs. To facilitate the delivery of the maximum amount of drugs to the urinary bladder, the rabbit's left femoral artery was ligated.

The bladder was exposed through a midline incision, and the bladder dome was catheterized with an 8 F catheter for both the monitoring of bladder pressure and for cystometry. The bladder neck-urethra was ligated to prevent micturition or leakage through the urethra. The catheter was connected to an infusion pump (Harvard Apparatus) and a pressure transducer.

Then, the rabbit was taken off of the isoflurane and anesthesia was maintained by ketamine-xylazine so that micturition reflexes could be observed during cystometry. After 15 minutes, the infusion pump was turned on and at an infusion rate of 1.0 mL/minute, a cystometric curve was generated. The volume at which a micturition reflex was observed was considered to be the functional capacity of the bladder. Bladder capacity and Bladder Compliance were determined. The bladder was then filled to 20 mL.

Intra-Arterial Pharmacological Agents Administration

Acetylcholine (Ach), a chemical that causes the bladder muscle (detrusor) to squeeze or contract, was injected through the intra-arterial polyethylene catheter in a volume of 0.31-0.39 mL (i.e., 0.1 mL/kg of rabbit), followed by 0.2 mL of heparinized saline. Change of intravesical pressure following the administration of Ach ($10^{-6}$ mol/kg) was monitored by the pressure transducer and recorded on a Grass model 7D polygraph. A 10-minute interval passed between Ach administrations, and three flushes of normal saline, in an amount of 0.1 ml/kg of rabbit, were administered. Three responses to Ach were performed at 10-minute intervals to ensure consistent responses.

After the third Ach administration, the application of the oxybutynin containing gel was administered to the vagina and the responses to Ach were determined at 15-minute intervals for 2 hours. When the response to Ach was reduced, then the time period was extended to 4 hours. At the end of the experiment, a second cystometric curve was generated.

1 mL of blood was collected at different points in time: immediately prior to the gel administration, at 15 minutes following administration of Oxybutynin, at 30-minute intervals thereafter for the duration of the experiment, and after the final cystometry. Then, the rabbit was euthanized.

Results

FIGS. 1A, B, and C show representative tracings of the effect of the high-dose Oxybutynin (0.5 g Oxybutynin/g gel) on the response to Ach. FIG. 1A shows a control response of the bladder and blood pressure to Ach. There is a rapid fall in blood pressure with a simultaneous increase in bladder pressure. FIG. 1B shows the effect of the administration of Ach 15 minutes after a high dose of Oxybutynin has been administered. There is a clear response of the blood pressure to the administration of Ach, but the response of the bladder is completely lost. Thus, the Oxybutynin was able to decrease the bladder pressure upon the administration of Ach. FIG. 1C shows the response 4 hours after Oxybutynin was administered. The bladder pressure still did not increase after the administration of Ach, while the blood pressure decreased.

Thus, the administration of the high-dose Oxybutynin formulation resulted in a significant decrease in Bladder Compliance since the bladder pressure was lower after the administration of oxybutynin than it was prior to the administration and an increase in bladder volume at micturition.

Figure 2C:
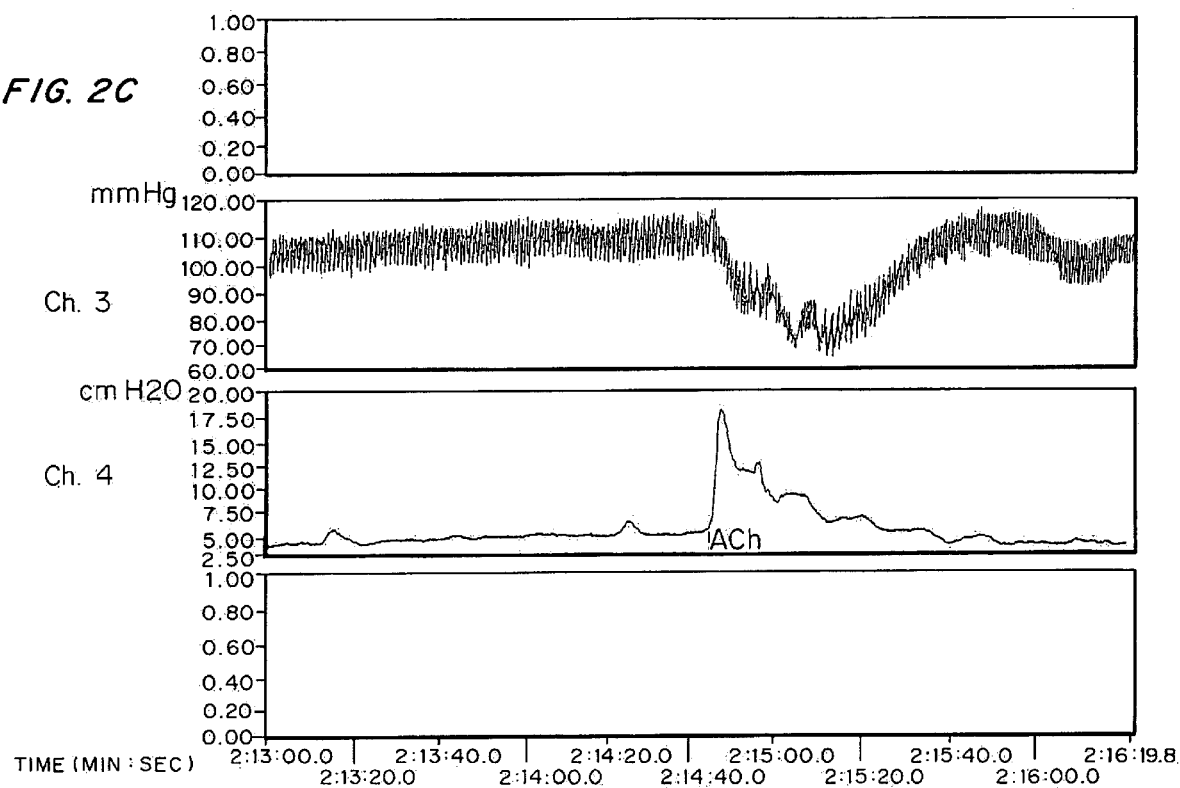
FIG. 2C shows the response 4 hours after a low dose of Oxybutynin was administered.

FIGS. 2A, B, and C show the response to a low dose of Oxybutynin. FIG. 2A shows a control response of the bladder and blood pressure to Ach. It demonstrates a significant Ach response in both the blood pressure and bladder pressure. FIG. 2B depicts the response effect to Ach 15 minutes after a low dose of Oxybutynin (0.05 g Oxybutynin/g gel) was administered. FIG. 2C shows the response 2 hours after Oxybutynin was administered. In two out of three experiments, there was no significant effect of the low dose on either the blood or bladder pressure. However in one experiment, the response of the bladder pressure to Ach was reduced by about 50% (individual results not shown).

These results show that vaginally delivered high-dose. Oxybutynin significantly reduced the contractile response of the bladder to Ach without having any significant effects on the response of the blood pressure to Ach.

Example 2

Study of the Effect of Vaginal Oxybutynin on Bladder Function Using Rabbits

The protocol described in Example 1 was followed in this experiment, with the following changes. The infusion pump was turned on and, at an infusion rate of 1.42 mL/minute, a cystometric curve was generated.

Results

Figure 3A:
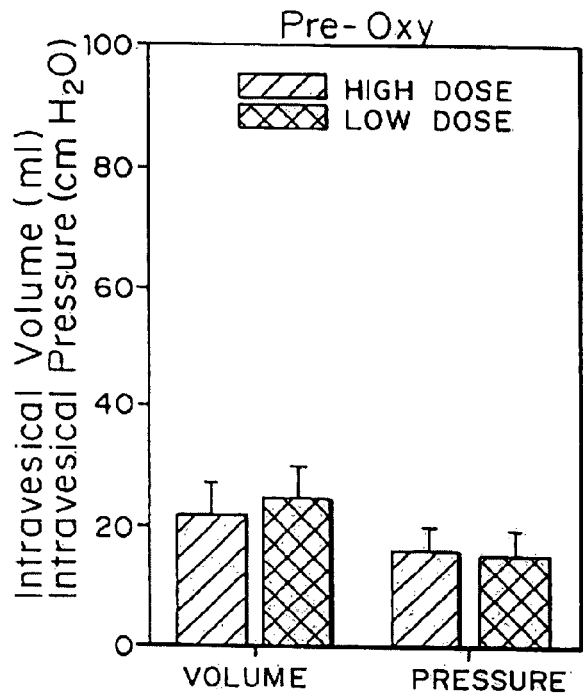
FIG. 3 is a bar graph of the effect of vaginally administered oxybutynin on the intravesical volume (mL) at micturition and the pressure (cm $H_2O$) at this volume.
Figure 3B:
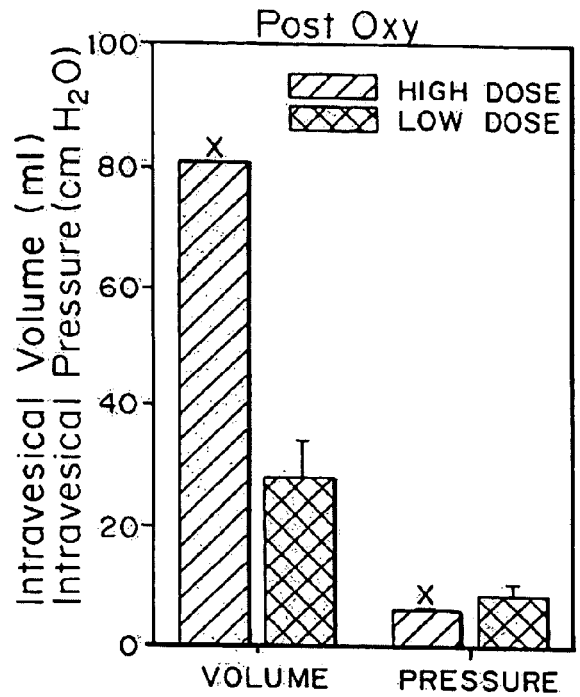

FIG. 3 presents the effect of vaginally administered oxybutynin on the intravesical volume (mL) at micturition and the pressure (cm $H_2O$) at this volume. Prior to the administration of oxybutynin, the mean volume at micturition was approximately 20 mL, and the intravesical pressure at this volume was approximately 16 cm of water. The high dose of oxybutynin resulted in a significant decrease in Bladder Compliance. The rabbits given the high dose of oxybutynin did not show micturition reflex up to a bladder volume of 80 mL, at which time the cystometry was stopped to avoid over-distension.

The low dose of oxybutynin also resulted in a decrease in Bladder Compliance. Micturition was observed at approximately the same volume after low dose treatment as before (about 22 mL), although the pressure at which micturition occurred was reduced from about 16 cm $H_2O$ before the administration of low dose Oxybutynin to about 8 cm $H_2O$ after the administration.

Figure 4A:
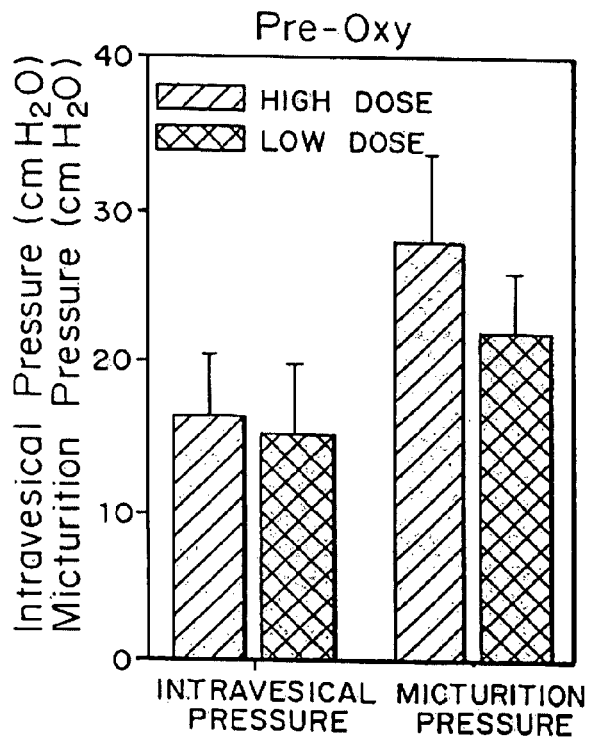
FIG. 4 is a bar graph of the effect of high and low doses of vaginally administered oxybutynin on the intravesical pressure (cm $H_2O$) at micturition and the micturition pressure (cm $H_2O$). The intravesical pressure is the pressure at which the, micturation reflex occurs. The micturition pressure is the maximum pressure generated during a micturition reflex contraction.
Figure 4B:
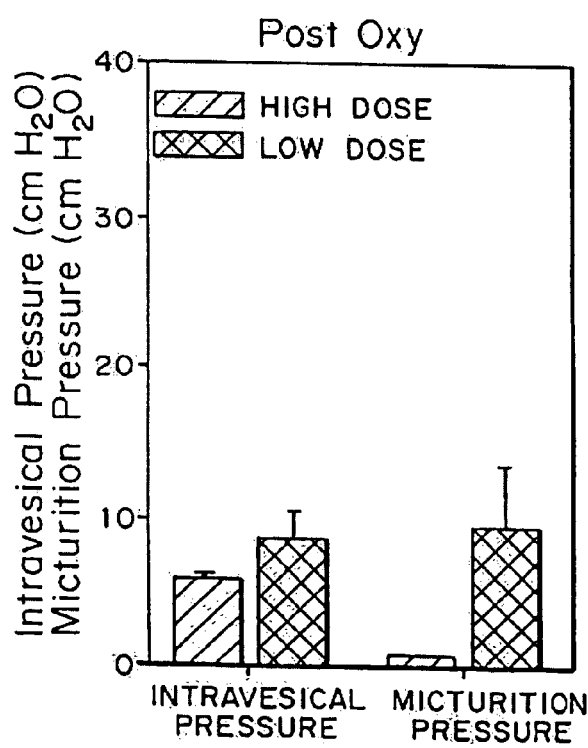

FIG. 4 presents a comparison of the intravesical pressure at micturition and the micturition pressure. The high dose resulted in decreased intravesical pressure during cystometry and inhibited the micturition reflex. Thus, at a bladder volume of 80 mL, the point at which cystometrey was stopped, there was no micturition reflex. The low dose also resulted in decreased intravesical pressure during cystometry (from about 15 cm $H_2O$ before administration to about 8 cm $H_2O$ after administration) and decreased the magnitude of the micturition reflex (from about 22 cm $H_2O$ before administration to about 10 cm $H_2O$ after administration). This relationship between the intravesical pressure and the magnitude of the micturition reflex is expected. If the pressure at micturition is reduced, the magnitude of the micturition reflex also decreases.

Figure 5:
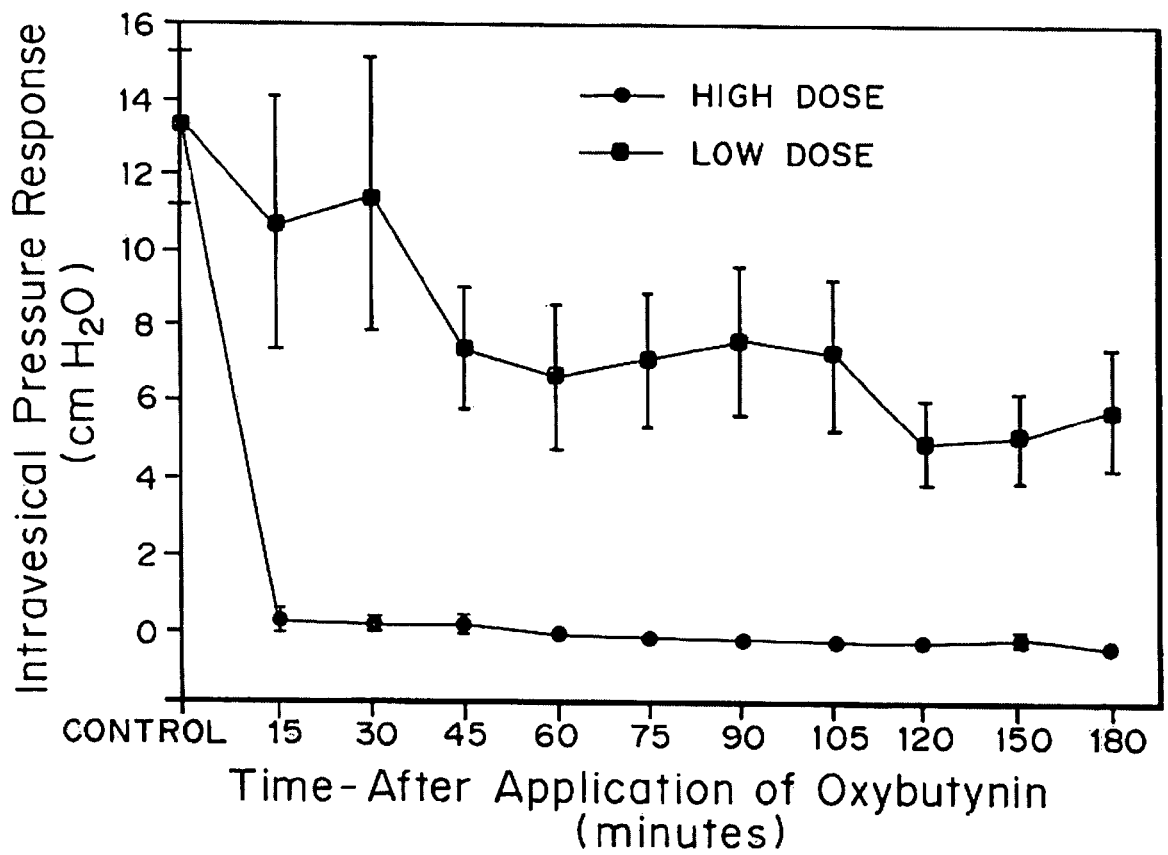
FIG. 5 is a graph of time after the application of oxybutynin (minutes) versus intravesical pressure (cm $H_2O$).

FIG. 5 presents the effect of oxybutynin on the contractile response to intra-arterial Ach. The high dose resulted in a complete inhibition at 15 minutes and the response was not restored after 4 hours. Data in FIG. 5 are presented for up to 3 hours because only two of the four rabbits were observed for the full 4 hours. The low dose resulted in a decreased response at 45 minutes, and remained at approximately the same intravesical pressure (about 7 cm $H_2O$) for the remaining 2.25 hours.

There was no effect of either the high or low dose of oxybutynin on the vascular response to Ach over the entire 4-hour period.

There was no effect of the high dose of the free base form on the response to Ach.

Example 3

Delivery of High Dose Oxybutynin to Rabbits

High doses of oxybutynin were tested to demonstrate the maximal short-term effects on both the bladder and cardiovascular systems. 30 mature female New Zealand white rabbits (~4 kg) were separated into five groups of six rabbits each. Intra arterial administration of Ach was used as a model for hyperreflexia. The effects on intra arterial stimulated contraction were compared with effects on micturition pressure generation.

Surgical Preparation

Each rabbit was sedated with an intramuscular injection of ketamine-xylazine ((25 mg ketamine+6 mg xylazine)/kg rabbit) and anesthesia was maintained by isoflurane. After anesthesia, the right external carotid artery was cannulated for blood pressure monitoring. A polyethylene catheter (Intramedic) with an outer diameter of 0.043 inches was inserted through the rabbit's right femoral artery until it reached the lower abdominal aorta (approximately 0.5 Central Mutual above the bifurcation of the aorta). A heparizined saline (30 iu/mL) filled polyethylene catheter was used for intra-arterial administration of drugs. To facilitate the delivery of the maximum amount of drugs to the urinary bladder, the rabbit's left femoral artery was ligated.

The bladder was exposed through a midline incision, and the bladder dome was catheterized with an 8 F catheter for both the monitoring of bladder pressure and for cystometry. The bladder neck-urethra was ligated to prevent micturition or leakage through the urethra. The catheter was connected to an infusion pump (Harvard Apparatus) and a pressure tranducer. The right carotid artery was cannulated for monitoring blood pressure. Bladder pressure and blood pressure were recorded on a Grass model 7D Polygraph, and were simultaneously digitized using a Polyview A/D digital analytical system.

Cystometry

Cystometry was performed at 1.4 mL/min until a micturition contraction or a volume of 80 mL was obtained. After the first cystometry, Ach ($10^{-6}$ mol/kg) was injected through the intra-arterial polyethylene catheter in a volume of 0.1 ml/kg followed by three washes of 0.2 ml of heparinized saline. The blood pressure and bladder pressure responses were recorded and digitized.

After three consistent Ach tests, (i.e. responses within 20% of each other) the rabbits in the control group (Group 1) received a vaginal administration of 3 mL of gel (no oxybutynin); the rabbits in the high dose group (Group 2) received a vaginal administration of 1.5 g of oxybutynin suspended in 3 mL of gel; the rabbits in the intermediate dose group (Group 3) received 0.5 g of oxybutynin suspended in 3 mL of gel; the rabbits in the low dose group (Group 4) received a vaginal administration of 0.15 g of oxybutynin suspended in 3 mL of gel; and the rabbits in the oral dose group (Group 5) received 0.5 g of an oral preparation of oxybutynin dissolved in 3 mL of saline.

Ach was administered at 10 minute intervals for two hours, and then a second cystometry was performed. Ach administration continued at 10 minute intervals for a second two hour period, and then a final cystometry performed.

Statistical significance was determined using analysis of variance followed by Bonferroni test for individual differences. A $p<0.05$ was required for significance.

Results

Figure 6:
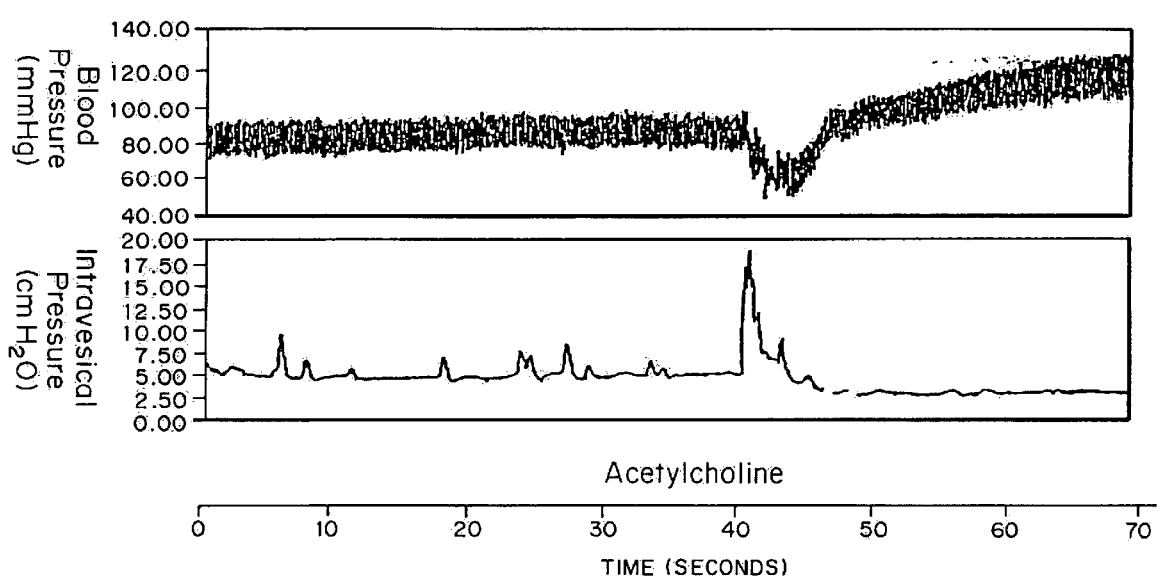
FIG. 6 is a cystometric curve of the blood pressure (mm Hg) and bladder pressure (cm $H_2O$) responses to acetylcholine (Ach) over time (seconds).

FIG. 6 displays a representative response of acetylcholine. As depicted in FIG. 6, Ach has effects on both blood pressure (mmHg) and bladder pressure (cm $H_2O$) over a time period of 70 seconds. These responses differentiate between the cardiovascular and bladder effects of oxybutynin. No significant alterations in either volume at micturition or micturition pressure were noted over the entire 4 hour experiment.

Figure 7:
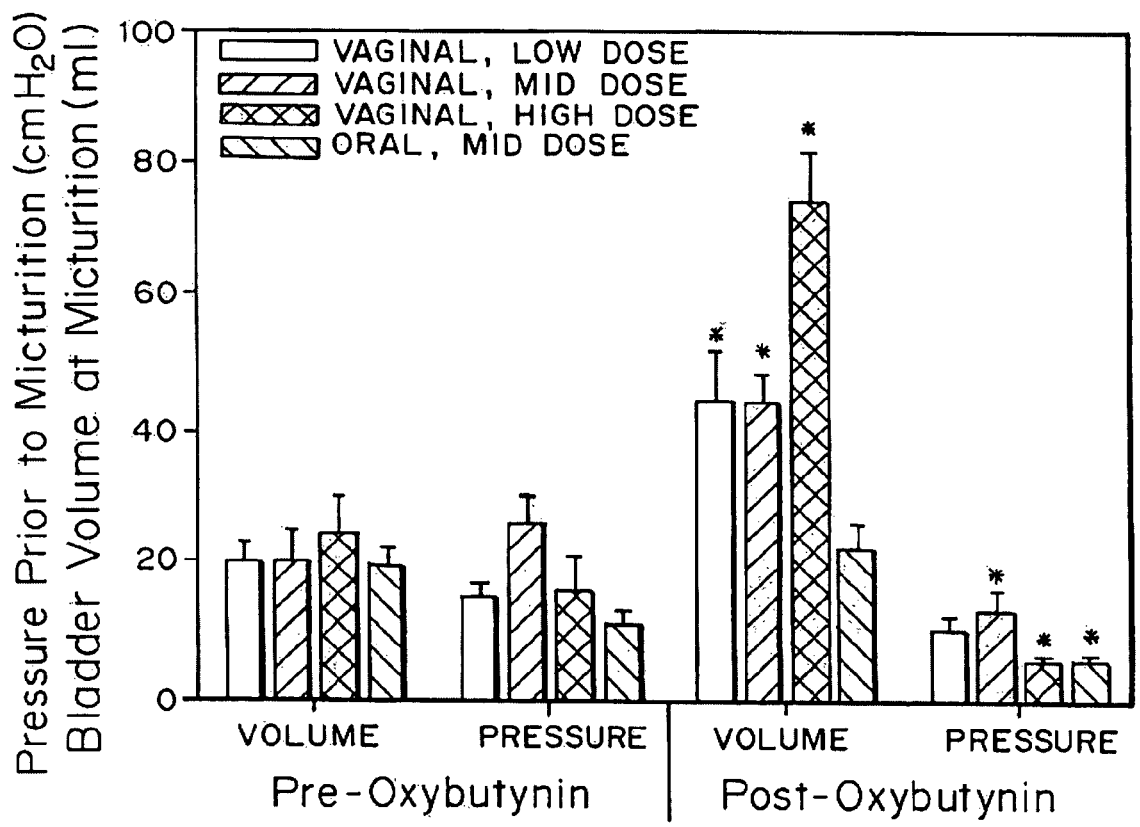
FIG. 7 is a bar graph of bladder capacity (mL) and pre-micturition pressure (cm $H_2O$) before and after the administration of different dosages and formulations of Oxybutynin. Each bar represents the mean ±SEM of between four and six rabbits. The "*" above a bar indicates that the post-oxybutynin result was significantly different from the pre-oxybutynin result. The clear bar relates to the vaginal, low dose Oxybutynin formulation. The bar with lines directed upwards to the right (///) relates to the vaginal, intermediate dose Oxybutynin formulation. The bar with crossed lines (xx) relates to the vaginal, high dose Oxybutynin formulation. The bar with lines directed upwards to the left (\\\) relates to the oral, intermediate dose Oxybutynin formulation.

FIG. 7 graphically depicts the increases in the functional bladder capacity (volume) at micturition and intravesical pressure prior to micturition following the vaginal administration of low, intermediate, and high doses of oxybutynin and an oral dose of oxybutynin. The low dose of oxybutynin had no significant effect on the intravesical pressure immediately prior to micturition, whereas the intermediate and high vaginal doses, and the oral administration of oxybutynin significantly reduced the intravesical pressure immediately prior to micturition (see FIG. 7). However, all of the formulations demonstrated a significant increase in the bladder volume at micturition. As a result of the increased volume in micturition and the reduced micturition pressure (for three of the groups), Bladder Compliance decreased in all oxybutynin-treated groups.

Figure 8:
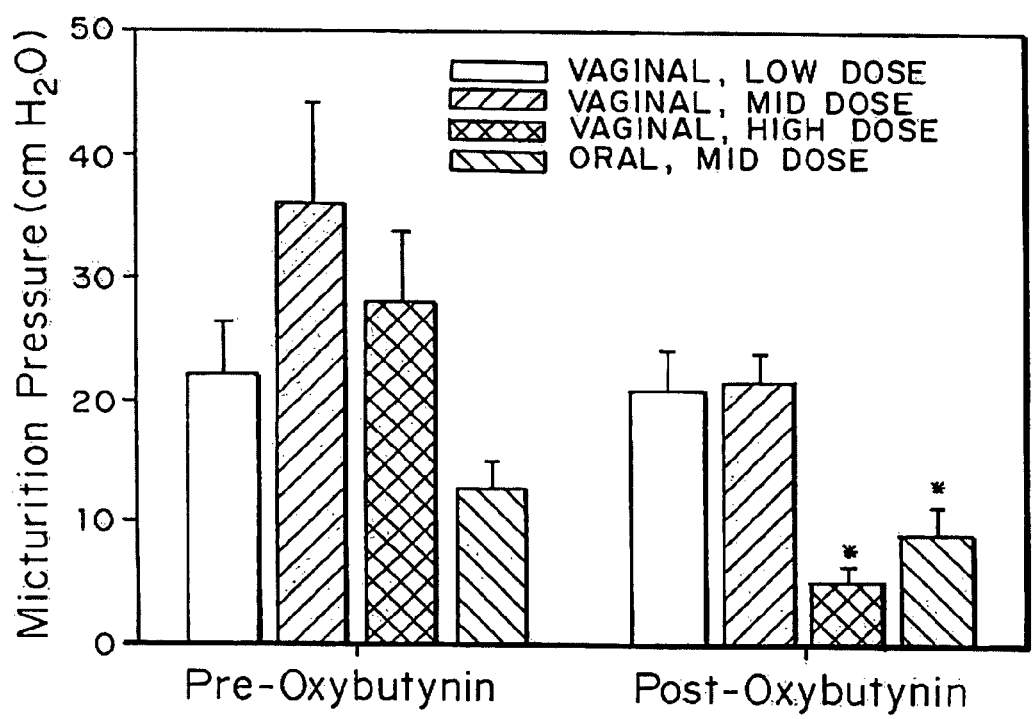
FIG. 8 is a bar graph of micturition pressure (cm $H_2O$) before and after the administration of different dosages and formulations of Oxybutynin. The post-oxybutynin administration values were obtained from a cytometry analysis performed four hours after the administration of the oxybutynin. Each bar represents the mean ±SEM of between four and six rabbits. The "*" above a bar indicates that the post-oxybutynin result was significantly different from the pre-oxybutynin result. The clear bar relates to the vaginal, low dose Oxybutynin formulation. The bar with lines directed upwards to the right (///) relates to the vaginal, intermediate dose Oxybutynin formulation. The bar with crossed lines (xx) relates to the vaginal, high dose Oxybutynin formulation. The bar with lines directed upwards to the left (\\\) relates to the oral, intermediate dose Oxybutynin formulation.

FIG. 8 is a bar graph of the effect of different formulations and dosages of oxybutynin on the micturition pressure (cm $H_2O$). Micturition pressure was not significantly affected by low or intermediate doses of vaginal oxybutynin. However, it was significantly reduced following the administration of both high vaginal oxybutynin and oral oxybutynin formulations (see FIG. 8). The cystometric values of the group receiving the vaginal gel without oxybutynin did not change over the course of the 4 hour experiment.

Figure 9:
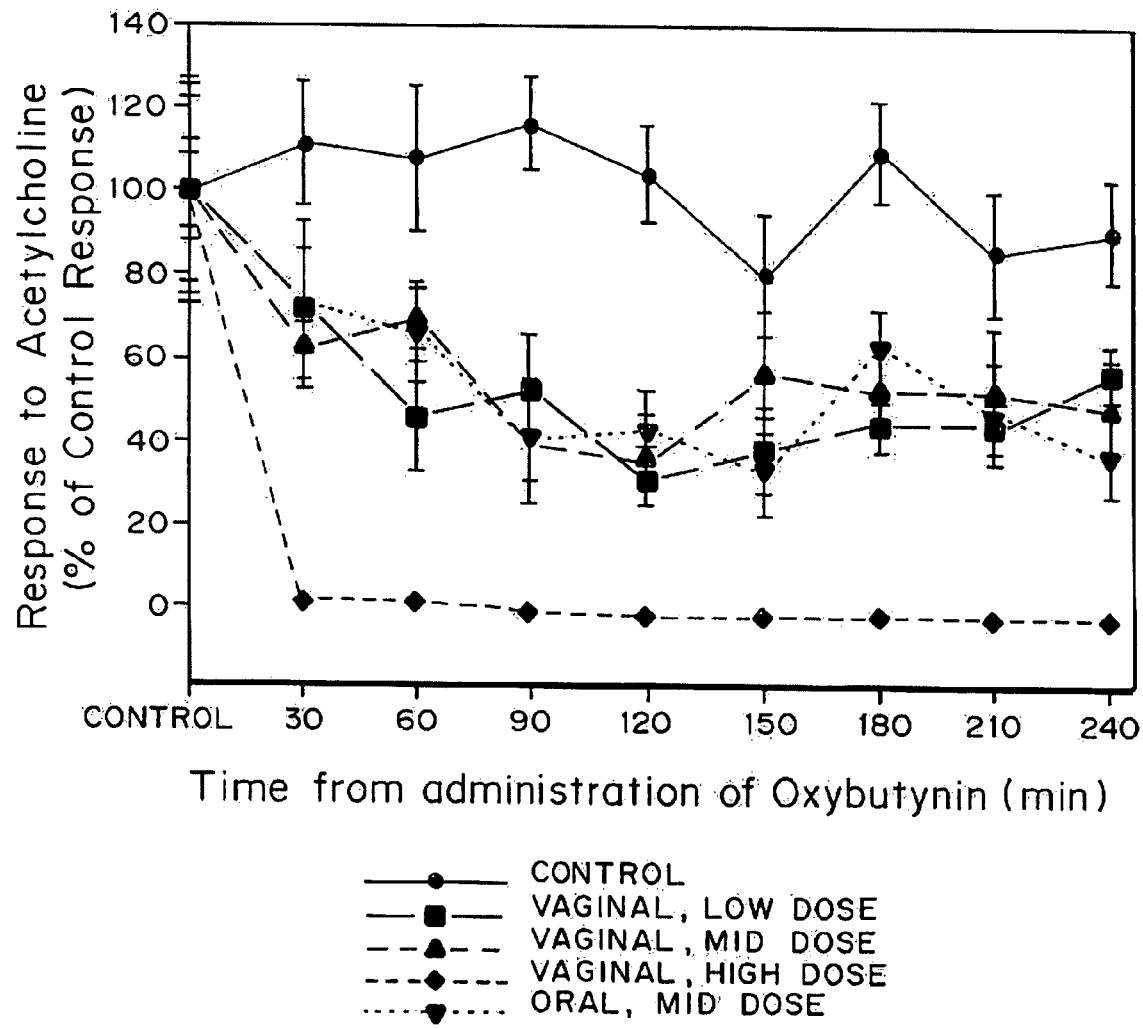
FIG. 9 is a graph of Response to Acetylcholine (% of controlled response) versus time following the administration of Oxybutynin (minutes) for different dosages and formulations of Oxybutynin. Each point on the graph represents the mean±SEM of between four and six rabbits. The circle (●) represents the control; the square (■) represents the vaginal, low dose of Oxybutynin; the triangle (▲) represents the vaginal, intermediate dose of Oxybutynin; the diamond (♦) represents the vaginal, high dose of Oxybutynin; and the upside down triangle (▼) represents the oral, intermediate dose of Oxybutynin.

FIG. 9 is a graph of time (minutes) versus response to Ach (% of control Response), which demonstrates the effect of different dosages and formulations of oxybutynin on the response to Ach. There were no statistically significant differences among any of the responses to Ach by the control formulations. All preparations of oxybutynin resulted in a statistically significant decrease in the response to Ach, compared to the control response (see FIG. 9).

High dose vaginal oxybutynin completely inhibited the response to Ach at 30 minutes following administration and remained active throughout the 4 hour study. Low and intermediate vaginal doses and oral oxybutynin resulted in a progressive decrease in the response to Ach reaching approximately 40% of control over 90 minutes, and remaining at this level for the rest of the experiment. There were no significant differences noted in the responses to these three preparations (FIG. 9).

There was no effect for any dose of vaginally delivered oxybutynin on the vascular response to Ach over the entire 4 hour period. The absence of an effect on the vascular response differentiates vaginally delivered oxybutynin from oral oxybutynin, which showed inhibitory effects on both the bladder and blood pressure responses to Ach.

Although the highest dose completely eliminated the response to acetylcholine and virtually eliminated the micturition reflex, only minor effects were observed on the cardiovascular system.

Summary of Results

Example 3 demonstrates that high dose vaginal oxybutynin is rapidly absorbed and the onset of action is very fast. Lower doses have slower onsets of action, and less severe effects.

Low, intermediate, and high dose vaginal oxybutynin formulations decreased Bladder Compliance by 3.3, 4.5, and 7.3 fold respectively. The decreased Bladder Compliances for the vaginal administrations were related to both increased functional bladder capacity and decreased intravesical pressure prior to micturition (for two of the formulations). The decrease in Bladder Compliance for the oral preparation was due solely to the decreased pressure prior to micturition. The magnitudes of the increased functional bladder capacities were well within the structural capacity of the bladder, and do not represent over-distension.

Vaginally administered oxybutynin in a gel preparation was effective at increasing Bladder Compliance, increasing functional capacity and decreasing the intravesical pressure at which a micturition reflex is generated. In addition, it was also effective at inhibiting Ach stimulated bladder contractions. At an oral concentration that had equal effects on Ach stimulated contraction as the intermediate dose of vaginal oxybutynin, the oral preparation had a smaller effect on Bladder Compliance and bladder capacity than the vaginal route of administration, and had significantly greater inhibitory effects on the micturition reflex.

Example 4

Clinical Studies

A 68 year old Caucasian female developed urgency incontinence two years after her laparoscopically assisted vaginal hysterectomy. The patient was then treated with DETROL® (2 mg) orally twice a day; and she experienced a slight improvement. Then, the medication was changed to Ditropan XL and Premarin vaginal cream (1 gm) every night, and she noticed additional improvement. However she experienced side effects, such as dry mouth, from the drug. Two weeks later, she started applying oxybutynin (5 mg) into the vagina at bed time, instead of Ditropan XL. Her urgency symptoms improved remarkably, and she did not experience any noticeable side effects. The patient used vaginal oxybutynin (5 mg) at bed time for 6 months. Throughout the treatment period, the drug remained effective at the lower dosage (5 mg) in controlling her symptoms of urgency incontinence, and she did not suffer from any side effects.

A 43 year old Caucasian female with a history of chronic pelvic pain and multiple surgical procedures, including pain mapping under conscious sedation and repair of occult bilateral inguinal hernias, developed urinary frequency, urgency and nocturia. Her urine analysis and urine culture were negative for signs of urinary tract infection. Her treatment began with vaginal oxybutynin (5 mg) once daily, at bed time, applied into the vagina. She noticed significant improvement. When the dose was increased to 5 mg of oxybutynin into the vagina twice daily, she noticed remarkable improvement of her symptoms and no significant side effects.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for treating urinary incontinence comprising administering into the vagina a dosage of a drug formulation wherein the active agent consists of between about 1 mg and about 20 of
a drug selected from the group consisting of tolterodine tartrate, propantheline, and oxybutynin hydrochloride, in a pharmaceutically acceptable carrier suitable for delivery through the vagina selected from the group consisting of topical ointment, cream, foam, gel, dry powder and aerosol, and providing immediate release of an effective amount of the drug to provide regionally effective drug levels which are less than the systemically effective levels of the drug, wherein the level is effective to increase bladder compliance, increase functional capacity and decrease the intravesical pressure at which a micturition reflex is generated.

2. The method of claim 1 wherein the carrier is selected from the group consisting of a gel.

3. The method of claim 1 wherein the drug is oxybutynin hydrochloride.

4. The method of claim 3 in a dosage effective to treat urinary incontinence in the absence of an effect on the vascular response.

5. The method of claim 1 wherein the drug is administered once or twice daily.

6. The method of claim 5 wherein the drug is oxybutynin hydrochloride in a gel for administration to the vagina.

7. The method of claim 3 wherein the oxybutynin hydrochloride is in an amount effective to inhibit acetycholine stimulated bladder contractions.

* * * * *

UNITED STATES PATENT AND TRADEMARK OFFICE
CERTIFICATE OF CORRECTION

| | | |
|---|---|---|
| PATENT NO. | : 8,226,972 B2 | Page 1 of 1 |
| APPLICATION NO. | : 10/324624 | |
| DATED | : July 24, 2012 | |
| INVENTOR(S) | : Gerianne Tringali DiPiano, John A. Ziemniak and Thomas Janicki | |

It is certified that error appears in the above-identified patent and that said Letters Patent is hereby corrected as shown below:

Title Page, Item (*) Notice, delete "This patent is subject to a terminal disclaimer".
Claim 1, column 11, line 22, insert --mg-- after "20".
Claim 2, column 12, lines 10-11, delete "selected from the group consisting of".

Signed and Sealed this
First Day of January, 2013

David J. Kappos
*Director of the United States Patent and Trademark Office*